(12) United States Patent
Macke et al.

(10) Patent No.: US 10,588,751 B2
(45) Date of Patent: Mar. 17, 2020

(54) IMPLANTS WITH FRANGIBLE FASTENER PORT PLUGS AND METHODS OF MANUFACTURING IMPLANTS WITH FRANGIBLE FASTENER PORT PLUGS

(71) Applicant: Zimmer, Inc., Warsaw, IN (US)

(72) Inventors: Jacob Macke, Warsaw, IN (US);
Robert D. Krebs, Warsaw, IN (US);
Adam Furore, Warsaw, IN (US)

(73) Assignee: Zimmer, Inc., Warsaw, IN (US)

(*) Notice: Subject to any disclaimer, the term of this patent is extended or adjusted under 35 U.S.C. 154(b) by 166 days.

(21) Appl. No.: 15/833,805

(22) Filed: Dec. 6, 2017

(65) Prior Publication Data

US 2018/0161163 A1    Jun. 14, 2018

Related U.S. Application Data

(60) Provisional application No. 62/432,948, filed on Dec. 12, 2016.

(51) Int. Cl.
*A61F 2/34* (2006.01)
*A61F 2/30* (2006.01)

(52) U.S. Cl.
CPC ...... *A61F 2/30771* (2013.01); *A61F 2/30744* (2013.01); *A61F 2/30767* (2013.01);
(Continued)

(58) Field of Classification Search
CPC .................. A61F 2/34; A61F 2/30744; A61F 2002/30561; A61F 2002/30784; A61F 2002/3093
See application file for complete search history.

(56) References Cited

U.S. PATENT DOCUMENTS

| 4,955,325 A | 9/1990 | Zarnowski et al. |
|---|---|---|
| 5,282,861 A | 2/1994 | Kaplan |

(Continued)

FOREIGN PATENT DOCUMENTS

| FR | 2826865 | 1/2003 |
|---|---|---|
| WO | 9515734 | 6/1995 |

(Continued)

OTHER PUBLICATIONS

Translation of WO 2018/024825 A1 (Year: 2019).*

(Continued)

*Primary Examiner* — Brian A Dukert
(74) *Attorney, Agent, or Firm* — Schwegman Lundberg & Woessner, P.A.

(57) ABSTRACT

An orthopedic implant can comprise a structural body, a plug and a frangible connection. The structural body can comprise a first surface, a second surface opposing the first surface, and a through-bore extending from the first surface to the second surface. The through-bore can have a bore surface. The structural body can be formed of a porous material. The plug can be disposed in the through-bore. The frangible connection can link the bore surface and the plug. A method of manufacturing an orthopedic implant can comprise producing a porous structural body having a port, producing a plug for positioning in the port, and producing a plurality of frangible crosspieces within the port to connect the plug to the structural body.

16 Claims, 5 Drawing Sheets

(52) U.S. Cl.
CPC ............ *A61F 2/30942* (2013.01); *A61F 2/34* (2013.01); *A61F 2002/3092* (2013.01); *A61F 2002/3093* (2013.01); *A61F 2002/30561* (2013.01); *A61F 2002/30682* (2013.01); *A61F 2002/30784* (2013.01); *A61F 2002/30981* (2013.01); *A61F 2002/3401* (2013.01); *A61F 2002/3429* (2013.01); *A61F 2310/00161* (2013.01); *A61F 2310/00544* (2013.01)

(56) References Cited

U.S. PATENT DOCUMENTS

| | | |
|---|---|---|
| 5,310,408 A | 5/1994 | Schryver et al. |
| 5,782,929 A | 7/1998 | Sederholm |
| 5,925,077 A | 7/1999 | Williamson et al. |
| 2003/0135281 A1 | 7/2003 | Hanssen |
| 2010/0057217 A1 | 3/2010 | Breimesser et al. |
| 2011/0270404 A1 | 11/2011 | Khan et al. |
| 2013/0310945 A1* | 11/2013 | Slone ............ A61F 2/34 623/22.34 |

FOREIGN PATENT DOCUMENTS

| | | | |
|---|---|---|---|
| WO | WO-2018024825 A1 * | 2/2018 | ............ A61F 2/34 |
| WO | 2018111651 A1 | 6/2018 | |

OTHER PUBLICATIONS

"International Application Serial No. PCT US2017 064927, International Search Report dated Apr. 24, 2018", 6 pgs.
"International Application Serial No. PCT US2017 064927, Written Opinion dated Apr. 24, 2018", 6 pgs.
"Australian Application Serial No. 2017376662, First Examination Report dated Jul. 31, 2019", 4 pgs.

* cited by examiner

IMPLANTS WITH FRANGIBLE FASTENER PORT PLUGS AND METHODS OF MANUFACTURING IMPLANTS WITH FRANGIBLE FASTENER PORT PLUGS

CLAIM OF PRIORITY

This application claims the benefit of priority to U.S. Provisional Application Ser. No. 62/432,948, filed on Dec. 12, 2016, which is incorporated herein by reference in its entirety.

TECHNICAL FIELD

This document pertains generally, but not by way of limitation, to orthopedic implant devices and methods of manufacturing orthopedic implant devices. More particularly, this disclosure relates, but not by way of limitation, to implants having features to allow for intraoperative modification of the implant, such as to customize fastening locations of the implant for a specific patient.

BACKGROUND

A natural joint, such as a hip joint or a shoulder joint, may undergo degenerative changes due to a variety of etiologies. When these degenerative changes become so far advanced and irreversible, it may ultimately become necessary to replace a natural joint with a prosthetic joint. For example, when implantation of a hip joint prosthesis becomes desirable, the head of the natural femur can be first resected and a cavity can then be created within the intramedullary canal of the host femur for accepting the hip prosthesis. The hip prosthesis may be inserted and supported within the host femur by cementing the hip prosthesis within the host femur or by using an impact method where the hip prosthesis is tightly fit within and is supported by the host femur. If the acetabulum also needs repair, all or most remnants of articular cartilage can be generally removed from the acetabulum and an acetabular prosthesis which will accommodate the head or ball of the hip prosthesis can be affixed to the acetabulum. The acetabular prosthesis can be affixed to the acetabulum by means of cement, screws or other appropriate fixation means.

An acetabular prosthesis can include an acetabular shell component and a polymeric shell liner. The acetabular shell component can be stabilized using fixation screws to secure the acetabular shell to bone. The acetabular shell component can include a smooth inner concave surface, a roughened outer convex surface and a plurality of holes or ports passing therethrough for receipt of the fixation screws. The fixation screws can be installed into all of the holes or only some of the holes depending on the geometry and biology of the anatomy of the patient. The polymeric shell liner can seat against the smooth inner concave surface and can act as a bearing surface for the head of the hip prosthesis.

As the hip prosthesis is loaded, micro-motion may occur between the acetabular shell component and the polymeric shell liner, potentially resulting in wear debris being formed between the shell component and the shell liner. Since some of the holes in the shell component may not receive fixation screws, the wear debris may pass through these open holes and out of the shell component.

Examples of acetabular prosthetic implants are described in U.S. Pat. No. 4,955,325 to Zarnowski et al., U.S. Pat. No. 5,310,408 to Schryver et al., U.S. Pat. No. 5,782,929 to Sederholm, U.S. Pat. No. 5,925,077 to Williamson et al., and U.S. Pub. No. 2010/0057217 to Breimesser et al.

OVERVIEW

The present inventors have recognized, among other things, that a problem to be solved can include the desire to plug fastener holes or ports in acetabular shells, or other orthopedic components, in order to increase the surface area of the acetabular shell to promote bone ingrowth, to prevent wear debris migration, and to prevent bone cement from flowing out of the shell. The present inventors have also recognized that there is a need for increasing the ease with which acetabular shell plugs can be adjusted to modify the number and location of ports in the acetabular shell. The present inventors have recognized that these problems and needs are particularly applicable to acetabular shells fabricated from porous material. For example, revision acetabular shells can be fabricated almost entirely from porous material, such as Trabecular Metal™. The open holes result in voids in the shell component that do not promote bone growth into the shell.

Conventional acetabular shells can include plugs that are attached to the fastener ports using mechanical fastening means, such as by using threading in the fastener port. These components typically require the surgeon to install plugs into a plurality of ports not used with fasteners, or to remove plugs from a plurality of ports that are to be used with fasteners, either of which can add time to the surgical procedure and can require the surgeon to perform dexterous procedures. Other acetabular shells have included sintered-in-place plugs that can be broken apart from the shell by the surgeon. One example is disclosed in U.S. Pat. No. 5,782,929 to Sederholm. These components, however, are limited in the materials the shell can be made of due to the sintering process. For example, solid sintered plugs can only be used with acetabular shells that are made with a solid metal portion to which the plug needs to be sintered. Sintering plugs into porous material, such as porous metal materials like Trabecular Metal™, can result in an insufficient bond between the plug and the shell.

The present subject matter can help provide a solution to various problems associated with plugging and unplugging of holes in prosthetic components by providing a frangible plug that can be made integrally with a shell, such as an acetabular shell. The plug can be an extension of the same material comprising the shell. The plug can be made of the same porous material as the shell. The plug can be attached via crosspieces connecting the plug and shell formed during manufacturing of the prosthetic component. The crosspieces can permit the plug to be held in place with sufficient strength, but can be easily broken to allow for removal of the plug without time consuming processes. The plug can be bonded in place by producing crosspieces comprising ligaments using a chemical vapor deposition (CVD) process. Additionally, the plug and shell can be made via a rapid manufacturing process that can incorporate the desired porosity and crosspieces comprising struts during the process for manufacturing the shell and plug.

In an example, the present subject matter can help provide a solution to this problem, such as by providing an acetabular shell that can comprise a cup-shaped body, a plurality of holes in the cup-shaped body, a plug and a plurality of crosspieces. The cup-shaped body can have an interior surface and an exterior surface. The plurality of holes can extend from the interior surface to the exterior surface so as to be able to permit fasteners to extend through the cup-shaped body. The plug can be disposed in each of the plurality of holes to prevent a fastener from extending through each of the plurality of holes. The plurality of crosspieces can connect each plug to one of the plurality of holes. Each crosspiece can be comprised of material contiguously defining the cup-shaped body and the plugs.

In another example, an orthopedic implant can comprise a structural body, a plug and a frangible connection. The structural body can comprise a first surface, a second surface opposing the first surface, and a through-bore extending from the first surface to the second surface, the through-bore having a bore surface. The structural body can be formed of a porous material. The plug can be disposed in the through-bore. The frangible connection can link the bore surface and the plug.

In yet another example, a method for a method of manufacturing an orthopedic implant can comprise producing a porous structural body having a port, producing a plug for positioning in the port, and producing a plurality of frangible crosspieces within the port to connect the plug to the structural body.

This overview is intended to provide an overview of subject matter of the present patent application. It is not intended to provide an exclusive or exhaustive explanation of the invention. The detailed description is included to provide further information about the present patent application.

DETAILED DESCRIPTION

Figure 1:
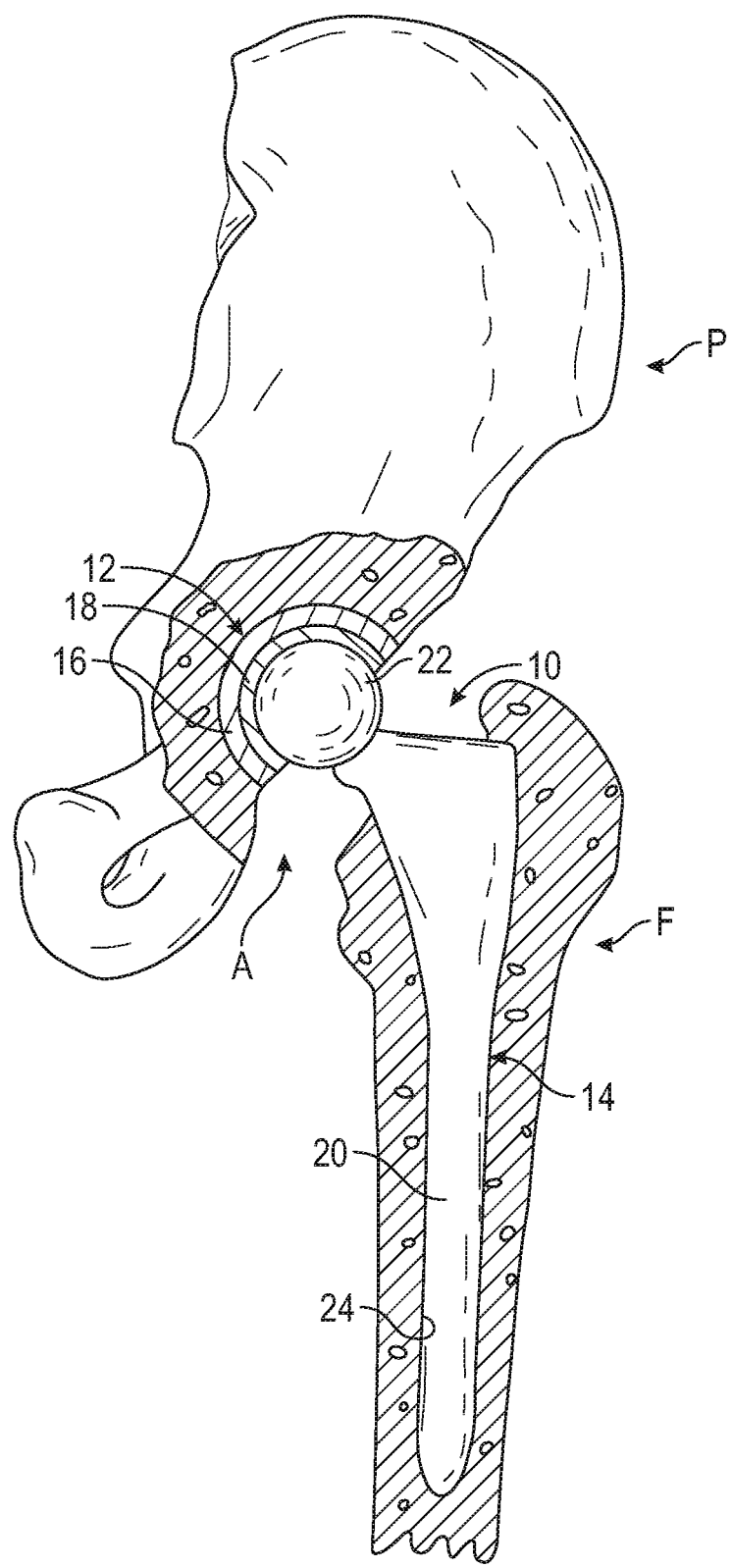
FIG. 1 is a partial sectional view of a hip joint and surrounding anatomy including an exemplary prosthetic implant system having an acetabular component and a femoral component.

FIG. 1 is a partial sectional view of a hip joint and surrounding anatomy including an exemplary prosthetic implant system 10 having acetabular component 12 and femoral component 14. The hip joint can include pelvis P and femur F. Acetabular component 12 can include acetabular shell 16 and prosthetic liner 18. Femoral component 14 can include stem 20 and head 22. Although the present disclosure is written with reference to a hip joint, prosthetic components for other joints, such as shoulders, can be made using the teachings of the present disclosure. For example, the teachings of the present disclosure can be applied to other anatomic features besides an acetabulum, such as a glenoid.

Acetabular component 12 can be received within a prepared acetabulum A of pelvis P. The prepared acetabulum can be reamed to remove unhealthy bone and to provide space for acetabular shell 16 and prosthetic liner 18. In other examples, acetabulum A is not prepared or is prepared with other bone-removal methods and tools. Femoral component 14 can be positioned within a prepared canal 24 of femur F. For example, femur F can be resected to accommodate head 22 and subsequently reamed to receive stem 20. Head 22 of femoral component 14 can be positioned to engage with acetabular component 12. In particular, head 22 can be configured to articulate within prosthetic liner 18. Thus, acetabular component 12 and femoral component 14 can reproduce construction and operation of a natural or anatomic hip joint.

Figure 2:
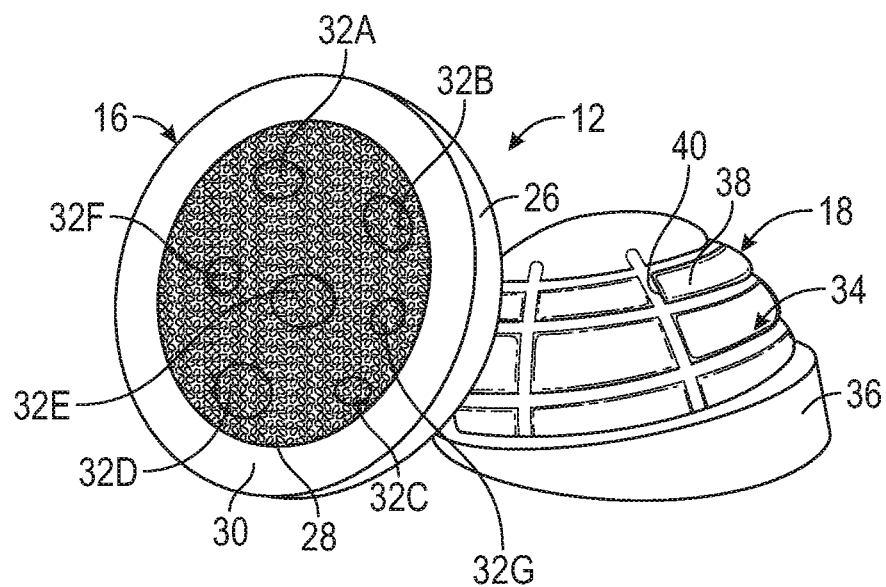
FIG. 2 is a perspective view of the acetabular component of FIG. 1 showing an acetabular shell and a prosthetic liner.

FIG. 2 is a perspective view of acetabular component 12 of FIG. 1 showing acetabular shell 16 and prosthetic liner 18. Acetabular shell 16 can include outer surface 26, inner surface 28, rim 30 and plugs 32A, 32B, 32C, 32D, 32E, 32F and 32G. Prosthetic liner 18 can include cup 34 and rim 36.

In the embodiment shown, outer surface 26 of acetabular shell 16 can be substantially hemispherical, though the shape of inner surface 26 may vary. Likewise, inner surface 28 can be substantially hemispherical so that the thickness of acetabular component 12 is approximately uniform, excepting for manufacturing tolerances and variations due to the porous nature of the material of acetabular component 12. However, in other embodiments, acetabular shell can have inner and outer surfaces that are matched to a specific patient, such as by configuring the surfaces to be mirror images of three-dimensional models or images of the anatomy of the specific patient.

Cup 34 of acetabular liner 18 can include outer surface 38 that can be configured to mate with inner surface 28 of acetabular shell 16. An inner surface (not shown) of cup 34 can be shaped to include a concavity that receives head 22 (FIG. 1). In examples, outer surface 38 and the inner surface comprising the concavity are substantially hemispherical and have matching equatorial and polar regions of acetabular shell 16. In other examples, cup 34 and acetabular shell 16 comprise portions of a sphere that are less than or greater than a hemisphere. Cup 34 provides a buffer or bearing surface between acetabular shell 16 and head 22. Cup 34 can be comprised of a biocompatible material, such as ultra-high molecular weight polyethylene (UHWMPE), for example, which is substantially rigid yet allows for flexibility and sliding of head 22. Rim 36 can be sized and shaped to facilitate insertion of cup 34 into acetabular shell 16 and to properly orientate prosthetic liner 18. The inner side (not shown) of rim 36 can also be configured to retain head 22. Outer surface 38 can include grooves 40 to facilitate engagement with inner surface 28 of acetabular cup shell 16. Outer surface 38 can be attached to acetabular shell 16 using bone cement. Plugs 32A-32G can prevent the bone cement from leaking out of acetabular shell 16 if not removed. The inner surface of cup 34 can be smooth to facilitate sliding of head 22.

Outer surface 26 and inner surface 28 can be opposing surfaces of a mono-block or monolithic mass or portion of material. In various examples, outer surface 26 and inner surface 28 can be fabricated from porous material to promote bone ingrowth from acetabulum A, among other reasons. Plugs 32A-32G can be integrally or natively included in the material of outer surface 26 and inner surface 28. As discussed in greater detail below, plugs 32A-32G can be fabricated separately from acetabular shell 16 and bonded in place with a material that forms at least a part of acetabular shell 16 and plugs 3A-32G, or can be produced simultaneously with acetabular shell 16. Rim 30 can be a separate piece or component added to the structure forming outer surface 26 and inner surface 28, or can be integrally or natively included in the material of outer surface 26 and inner surface 28.

The material forming plugs 32A-32G can be linked with the material forming the other portions of acetabular shell 16 between outer surface 26 and inner surface 28 by other portions of the material forming acetabular shell 16. In examples, plugs 32A-32G are connected to the other portions of acetabular shell 16 via crosspieces, which can take the form of ligaments, struts, rods, pins, webbing, and the like. The crosspieces can be made to be frangible so as to be readily breakable by a surgeon intraoperatively either by hand or by tool, such as a manually operated punch or a powered hand tool. The crosspieces can have various shapes and cross-sectional areas. The sum-total of the force needed to break all of the crosspieces connecting each of plugs 32A-32G to the remaining portions of acetabular shell, e.g., the respective port to which each plug is attached, can be lower than what the surgeon can provide either manually or with the aid of a manual or powered tool. As such, a surgeon can intraoperatively decide which of plugs 32A-32G to remove from acetabular shell 16 after evaluating the anatomy of acetabulum A (FIG. 1) of a specific patient, as shown in FIG. 3.

Figure 3:
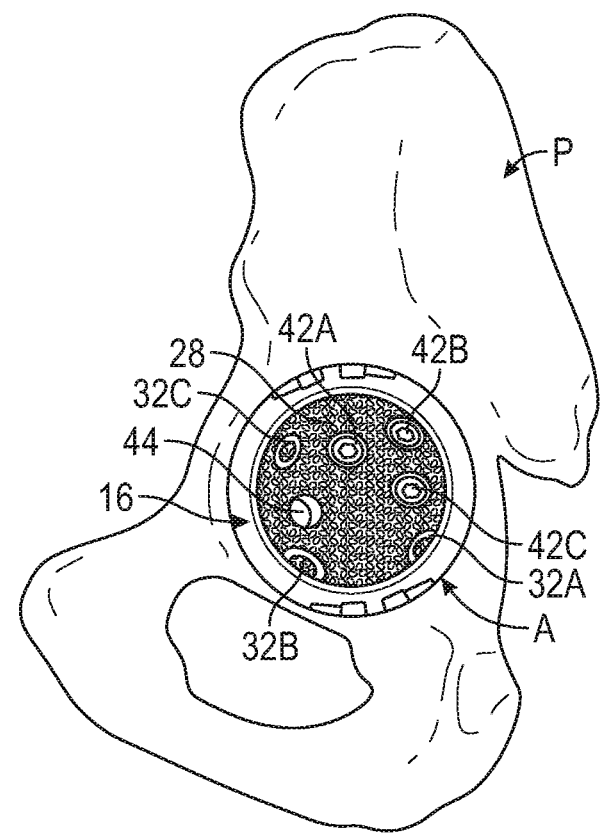
FIG. 3 is a schematic view of the acetabular component of FIG. 2 implanted in an acetabulum of a pelvis showing the acetabular shell having fastener ports with and without frangible plugs.

FIG. 3 is a schematic view of acetabular component 12 of FIG. 2 implanted in acetabulum A of pelvis P showing acetabular shell 16 including frangible plugs 32A, 32B and 32C, fasteners 42A, 42B and 42C, and fastener port 44. Frangible plugs 32A-32C can remain attached to acetabular shell 16 as originally positioned via the aforementioned crosspieces, as is shown in FIG. 2. Fastener port 44 can comprise an opening through acetabular shell 16 after frangible plug 32G (FIG. 2) has been removed from acetabular shell 16 via breakage of the ligaments. Fasteners 42A, 42B and 42C can comprise hardware inserted through fastener ports, similar to fastener port 44, after crosspieces have been broken to remove frangible plugs 32D-32F (FIG. 2).

FIG. 3 demonstrates that a surgeon can selectively remove one or more of frangible plugs 32A-32G from acetabular shell 16 in order to form fastener ports to receive fasteners. The surgeon can intraoperatively remove a selected sub-set of frangible plugs 32A-32G (or all of frangible plugs 32A-32G if desired) after comparing the location of frangible plugs 32A-32G to the anatomic features of pelvis P. In locations where the bony structure forming acetabulum A is weak or deficient, a sub-set of frangible plugs 32A-32G can remain in place. In locations where the bony structure is strong or healthy, a different sub-set of frangible plugs 32A-32G can be removed in order to produce ports for the reception of fasteners to secure acetabular shell 16 to acetabulum A. The discretion of the surgeon can be exercised to determine how many fasteners are desired to hold acetabular shell 16 in place and the locations of the fasteners, and which corresponding frangible plugs can be removed. Fasteners, such as fasteners 42A-42C can comprise any suitable fastener as is known in the art, such as threaded fasteners or screws. As is discussed below, the fastener ports, such as fastener port 44, can be shaped to mate with a head of a fastener and to receive threading of a fastener.

Frangible plugs 32A-32G can be configured to be removed intraoperatively by breaking of the crosspieces holding each of the plugs in place. For example, frangible plugs 32A-32G can be punched or twisted out by the surgeon using his or her hands or an appropriate tool. Acetabular shell 16 can be made of a variety of materials that are porous to promote bone ingrowth and that can be shaped to include the frangible crosspieces that can be broken away intraoperatively. In examples, acetabular shell 16 can be made via a chemical vapor deposition process to include ligaments made of a coating or film material, such as tantalum metal, as discussed with reference to FIGS. 4A-4C. In other examples, acetabular shell 16 can be made with a rapid manufacturing process to include struts made of a base or core material, such as titanium metal, as is discussed with reference to FIGS. 5A and 5B.

Figure 4A:
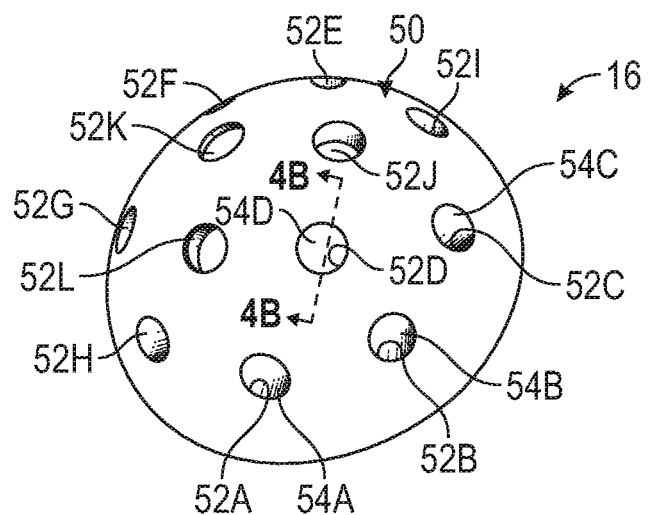
FIG. 4A is a schematic view of an embodiment of the acetabular shell of FIGS. 1-3 comprising a porous shell structure having fastener ports with frangible plugs produced by a chemical vapor deposition process.

FIG. 4A is a schematic view of an embodiment of acetabular shell 16 of FIGS. 1-3 comprising porous shell structure 50 having fastener ports 52A-52L with frangible plugs 54A-54D produced by a chemical vapor deposition (CVD) process. Additionally, frangible plugs 54E-54L (not illustrated) can be provided in fastener ports 52E-52L, respectively, but are not illustrated to more clearly show fastener ports 52E-52L.

Figure 4B:
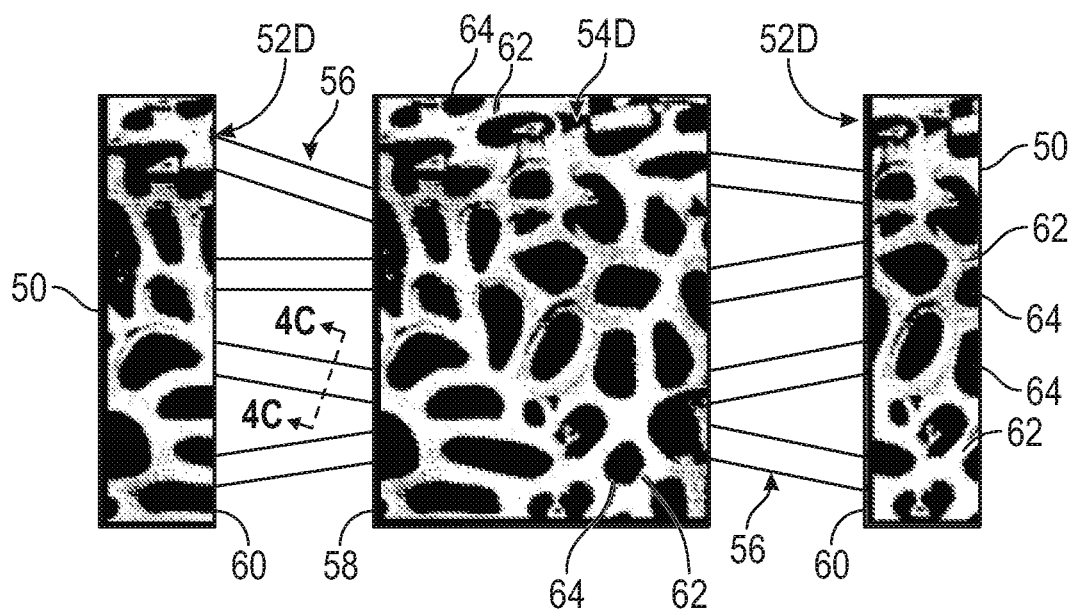
FIG. 4B is a schematic cross-sectional view of a frangible plug of FIG. 4A including film-coating ligaments made during a chemical vapor deposition process.

FIG. 4B is a schematic cross-sectional view of frangible plug 54D of FIG. 4A being held within fastener port 52D using film-coating ligaments 56 made during a chemical vapor deposition process. Frangible plug 54D can include sidewall 58 and fastener port 52D can include sidewall 60. Porous shell structure 50 and frangible plug 54D can have ligaments 62 interconnected to form open spaces 64.

Figure 4C:
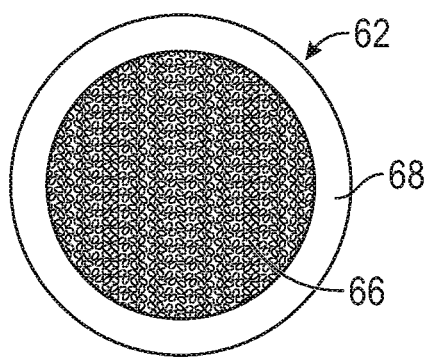
FIG. 4C is a schematic cross-sectional view of a film-coated ligament defining the porous material of the porous shell structure and frangible plug of FIGS. 4A and 4B.

FIG. 4C is a cross-sectional view of one of ligaments 62 of FIG. 4B. Each ligament 62 is formed by carbon core 66 covered by thin film 68 of metal such as tantalum, niobium or alloys of each. Ligaments 56 can be made of the material of thin film 68 during a CVD process. FIGS. 4A, 4B and 4C are discussed concurrently.

FIG. 4B is not drawn to scale in order to more readily visualize the features of acetabular shell 16. For example, the distance between sidewall 58 of frangible plug 54D and sidewall 60 of fastener port 52D is exaggerated to permit visualization of ligaments 56. Additionally, the number of ligaments 56 is fewer than can be used in practice. Likewise, the density of ligaments 56 can be greater in practice. Furthermore, the density of ligaments 62 can be greater in practice.

Porous shell structure 50 of acetabular shell 16 can be formed of a suitable material that promotes bone ingrowth and is biocompatible, such as porous metal, or a porous tantalum having a porosity as low as 55%, 65%, or 75% and as high as 80%, 85%, or 90%, for example. An example of a highly porous tantalum material is produced using Trabecular Metal™ Technology generally available from Zimmer Biomet, of Warsaw, Ind. Trabecular Metal™ is a trademark of Zimmer Biomet. Such a material may be formed from a reticulated vitreous carbon foam substrate which is infiltrated and coated with a biocompatible metal, such as tantalum, by a chemical vapor deposition (CVD) process in the manner disclosed in detail in U.S. Pat. No. 5,282,861 to Kaplan, the disclosure of which is expressly incorporated herein by reference in its entirety for all purposes. In addition to tantalum, other metals such as niobium, or alloys of tantalum and niobium with one another or with other metals may also be used.

FIG. 4B shows porous shell structure 50 and frangible plug 54D comprising an open cell tantalum structure that can be used as the material for acetabular shell 16. The open cell metal structures can be fabricated using the tantalum metal film and carbon substrate combination, with the film deposited by CVD, which mimics bone closely in having ligaments 62 interconnected to form open spaces 64. With the variables available in both the materials and the fabrication process, e.g., carbon core 66 and thin film 68, it is possible to obtain the simultaneous optimization of multiple properties (e.g. strength, stiffness, density, weight) in ligaments 62 and ligaments 56 for the given application of substitution for bone. Although plug 54D is shown as being porous in the form of an open cell tantalum structure, it is contemplated that in other examples solid plugs can be used with the porous shell structures described herein.

Generally, the porous tantalum structure can include a large plurality of ligaments 62 defining open spaces 64 therebetween, with each ligament 62 generally including a carbon core 66 covered by a thin film 68 of metal such as tantalum, for example. Open spaces 64 between ligaments 62 form a matrix of continuous channels having no dead ends, such that growth of cancellous bone through the porous tantalum structure is uninhibited. The porous tantalum may include up to 75%-85% or more void space therein. Thus, porous tantalum is a lightweight, strong porous structure which is substantially uniform and consistent in composition, and closely resembles the structure of natural cancellous bone, thereby providing a matrix into which cancellous bone may grow to provide fixation of acetabular component 12 to bone.

The porous tantalum structure may be made in a variety of densities in order to selectively tailor the structure for particular applications. In particular, as discussed in the above-incorporated U.S. Pat. No. 5,282,861, the porous tantalum may be fabricated to virtually any desired porosity and pore size, and can thus be matched with the surrounding natural bone in order to provide an improved matrix for bone ingrowth and mineralization. Furthermore, the density of the porous tantalum may be made to have varying densities within porous shell structure 50 and frangible plugs 54A-54L to provide various features to acetabular shell 16, as is further discussed with reference to FIGS. 5A-5C.

With reference to FIG. 4B, ligaments 56 can be formed by via a chemical vapor deposition process used to bond frangible plug 54D to porous shell structure 50. Frangible plug 54D and porous shell structure 50 can be produced via a separate or first CVD process as described in the above-incorporated U.S. Pat. No. 5,282,861. Porous shell structure 50 can be fabricated with ports 52A-52L being open, and frangible plugs 54A-54L can be fabricated separately. Thereafter, frangible plugs 54A-54L can be inserted into ports 52A-52L and an additional or second CVD process can be conducted to produce ligaments 56 out of the material of film 68. In such a process, carbon cores 66 of frangible plugs 54A-54L and porous shell structure 50 are coated twice with thin film 68.

Alternatively, just the material of carbon core 66 can be used to initially from the shapes of frangible plugs 54A-54L and porous shell structure 50, frangible plugs 54A-54L can be inserted into ports 52A-52L, and a single CVD process can be used to simultaneous coat the carbon core material of frangible plugs 54A-54L and porous shell structure 50 while simultaneously producing ligaments 56.

Ligaments 56 can thus be produced to readily hold frangible plug 54D in fastener port 52D. Each of ligaments 56 can be configured to be strong enough, e.g., either dense enough or thick enough, to withstand installation and use of acetabular component 12. Additionally, the total number and density of ligaments 56 can be varied to control the bonding strength between fastener port 52D and frangible plug 54D. Ligaments 56 can be configured to hold frangible plug 54D in place while acetabular shell 16 is impacted by an installation tool, such as for insertion into acetabulum A (FIG. 3). Ligaments 56 can additionally be configured to allow a surgeon to break ligaments 56 holding frangible plug 54D in place to allow frangible plug 54D to be removed from porous shell structure 50. For example, ligaments 56 can be configured to sheer when frangible plug 54D is subjected to rotational force. Frangible plugs 54A-54L can be configured to include a bore or socket, e.g. a hexagonal socket, to receive a tool to facilitate punching or twisting of frangible plugs 54A-54L for removal.

Prosthetic components with porous structures including ligaments and the like that provide frangible coupling between removable plugs and a base structure, such as the ones described herein, can be provided by any number of suitable three-dimensional, porous structures, and these structures can be formed with one or more of a variety of materials including but not limited to polymeric materials which are subsequently pyrolyzed, metals, metal alloys, ceramics. In some instances, a highly porous three-dimensional structure will be fabricated using a selective laser sintering (SLS) or other additive manufacturing-type process such as direct metal laser sintering. In one example, a three-dimensional porous article is produced in layer-wise fashion from a laser-fusible powder, e.g., a polymeric material powder or a single-component metal powder, that is deposited one layer at a time. The powder is fused, remelted or sintered, by the application of laser energy that is directed to portions of the powder layer corresponding to a cross section of the article. After the fusing of the powder in each layer, an additional layer of powder is deposited, and a further fusing step is carried out, with fused portions or lateral layers fusing so as to fuse portions of previous laid layers until a three-dimensional article is complete. In certain embodiments, a laser selectively fuses powdered material by scanning cross-sections generated from a 3-D digital description of the article, e.g., from a CAD file or scan data, on the surface of a powder bed. Net shape and near net shape constructs are infiltrated and coated in some instances.

Complex geometries can be created using such techniques. In some instances, a three-dimensional porous structure will be particularly suited for contacting bone and/or soft tissue, and in this regard, can be useful as a bone substitute and as cell and tissue receptive material, for example, by allowing tissue to grow into the porous structure over time to enhance fixation (i.e., osseointegration) between the structure and surrounding bodily structures, for example, to provide a matrix approximating natural cancellous bone or other bony structures. In this regard, a three-dimensional porous structure, or any region thereof, may be fabricated to virtually any desired density, porosity, pore shape, and pore size (e.g., pore diameter). Such structures therefore can be isotropic or anisotropic. Such structures can be infiltrated and coated with one or more coating materials. When coated with one or more biocompatible metals, any suitable metal may be used including any of those disclosed herein such as tantalum, titanium, a titanium alloy, cobalt chromium, cobalt chromium molybdenum, tantalum, a tantalum alloy, niobium, or alloys of tantalum and niobium with one another or with other metals. Illustratively, a three-dimensional porous structure may be fabricated to have a substantially uniform porosity, density, pore shape and/or void (pore) size throughout, or to comprise at least one of pore shape, pore size, porosity, and/or density being varied within the structure. For example, a three-dimensional porous structure to be infiltrated and coated may have a different pore shape, pore size and/or porosity at different regions, layers, and surfaces of the structure. According to certain embodiments of the present disclosure, regions of a three-dimensional porous structure to be infiltrated and coated may have a porosity as low as 55%, 65%, or 75% or as high as 80%, 85%, or 90%, or within any range defined between any pair of the foregoing values. In some embodiments, a non-porous or essentially non-porous base substrate will provide a foundation upon which a three-dimensional porous structure will be built and fused thereto using a selective laser sintering (SLS) or other additive manufacturing-type process. Such substrates can incorporate one or more of a variety of biocompatible metals such as titanium, a titanium alloy, cobalt chromium, cobalt chromium molybdenum, tantalum, or a tantalum alloy.

In various embodiments, acetabular shell 16 can be fabricated from material compatible with various rapid manufacturing processes. For example, acetabular shell 16 can be fabricated from lasered metallic powder, as discussed with reference to FIGS. 5A-5C.

Figure 5A:
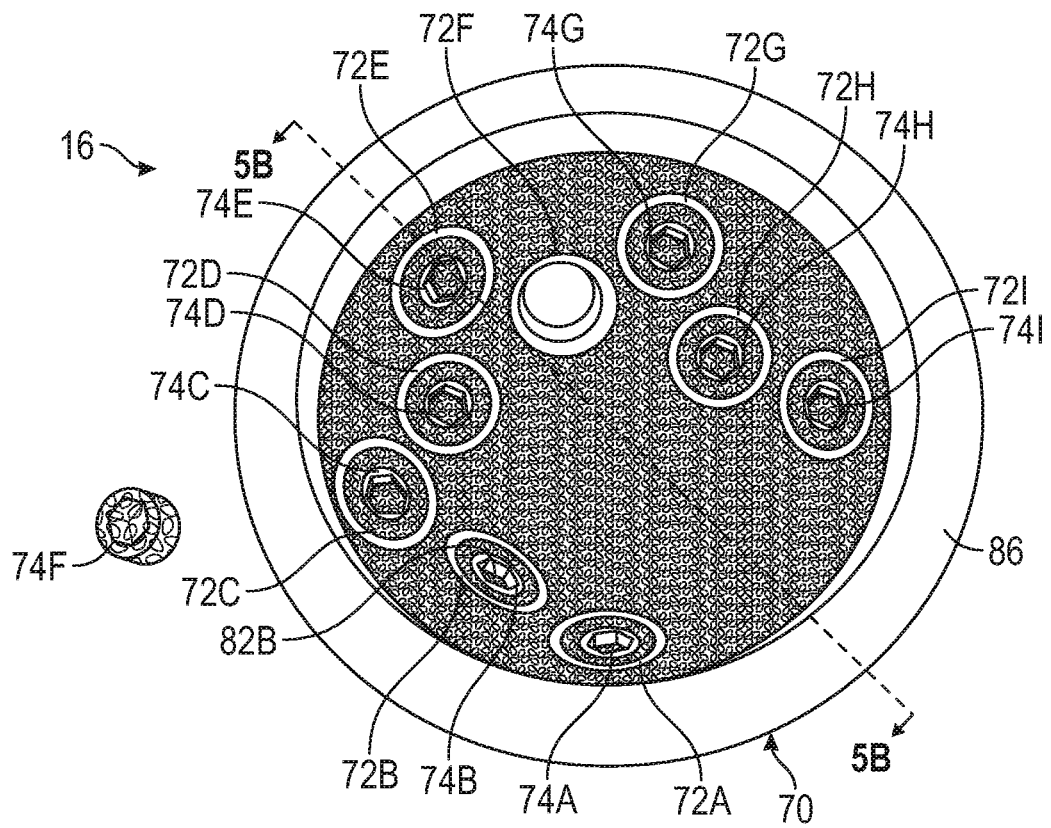
FIG. 5A is a schematic view of an embodiment of the acetabular shell of FIGS. 1-3 comprising a porous shell structure having fastener ports with frangible plugs produced by an additive manufacturing process.
Figure 5B:
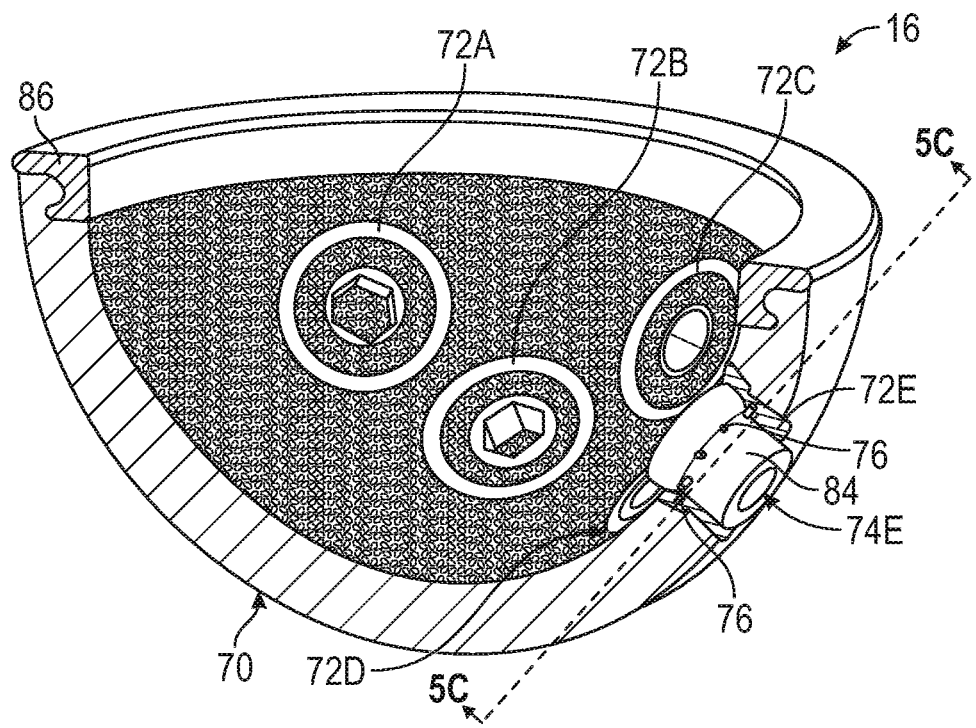
FIG. 5B is a schematic cross-sectional view of the acetabular shell of FIG. 5A showing porous material having portions with porosity of differing density.
Figure 5C:
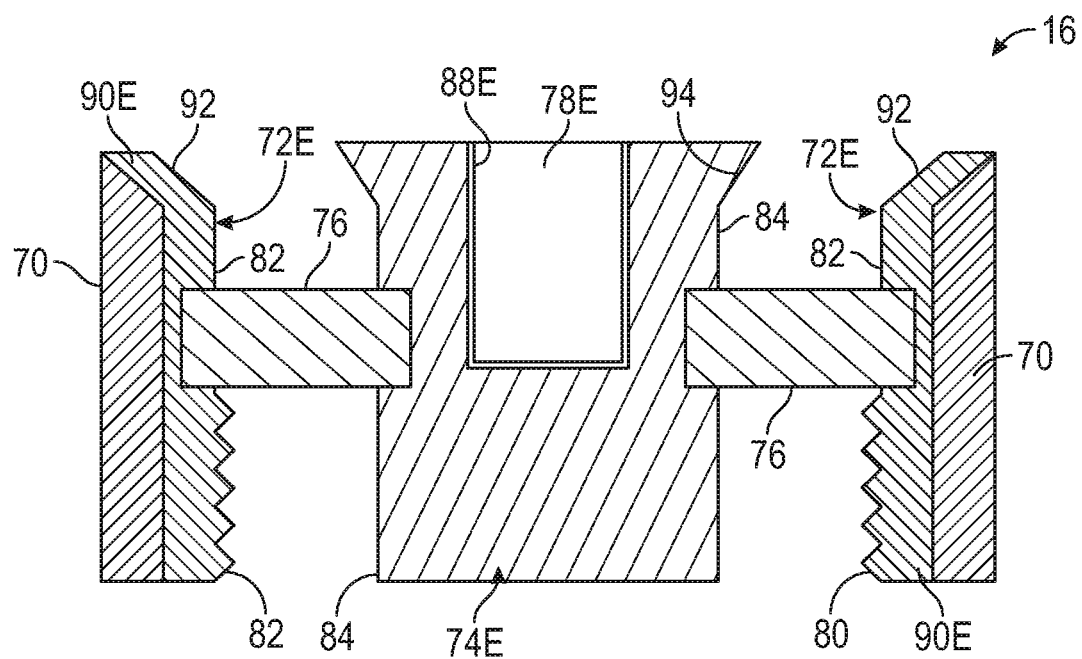
FIG. 5C is a schematic cross-sectional view of a frangible plug of FIG. 5B showing frangible struts, a removal socket and threading.

FIG. 5A is a schematic view of an embodiment of acetabular shell 16 of FIGS. 1-3 comprising porous shell structure 70 having fastener ports 72A-72I with frangible struts 74A-74I produced by an additive manufacturing process. FIG. 5B is a schematic cross-sectional view of acetabular shell 16 of FIG. 5A showing porous material of shell structure 70 and frangible plug 74E having portions with porosity of differing density. FIG. 5C is a schematic cross-sectional view of frangible plug 74E of FIG. 5B showing frangible struts 76, removal aperture 78E and threading 80. Fastener port 72E can include sidewall 82 and frangible plug 74E can include sidewall 84. Porous shell structure 70 can have rim 86 attached to an edge of the hemispherical shape in order to protect the porous material of acetabular shell 16 and to provide a smooth finish to the edge of acetabular shell 16. FIG. 5C is not drawn to scale as discussed with reference to FIG. 4B. FIGS. 5A, 5B and 5C are discussed concurrently.

Porous shell structure 70, frangible plug 74E and struts 76 can be configured to operate in a similar manner as porous shell structure 50, frangible plug 54D and ligaments 56 of FIGS. 4A-4C. Specifically, frangible plug 74E can be configured to be attached to porous shell structure 70 using struts 76 such that frangible plug 74E can be removed from acetabular shell 16 by a surgeon intraoperatively by breaking struts 76. However, the material of porous shell structure 70, frangible plug 74E and struts 76 can be arranged differently. Porous shell structure 70, frangible plug 74E and struts 76 can be made of the same contiguous body of material such that acetabular shell 16 has uniform, or nearly so depending on manufacturing variances, composition throughout. Although plug 54D is shown as being porous in the form of a spaced titanium structure, it is contemplated that in other examples solid plugs can be used with the porous shell structures described herein.

In examples, the material of porous shell structure 70, frangible plug 74E and struts 76 can comprise titanium that is fabricated using a rapid manufacturing process. In examples, the rapid manufacturing process can comprise an additive manufacturing process, such as a powder deposition process. In such a process, very thin layers (e.g., layers that are only as thick as several levels of particles of the powdered titanium) of powdered titanium can be laid down incrementally. At each increment, selective portions of the powdered titanium can be solidified to form a portion of acetabular shell 16. For example, a laser can be used to selectively melt portions of the powdered titanium layer that will form acetabular shell 16. Subsequently, a new layer of titanium powder particles can be laid down on top of the previous, partially solidified layer and an additional solidification process can occur. The steps can be repeated until acetabular shell 16 is built-up from one end to the other. Other types of rapid manufacturing processes can be used to fabricate acetabular shell, such as 3D printing processes.

The rapid manufacturing processes can be used to include a desired level of porosity directly into porous shell structure 70, frangible plug 74E and struts 76. Likewise, struts 76 can be made to have any desired shape, size, number and aggregate strength and density in order to generate sufficient bonding strength to survive implantation and operation of acetabular shell 16, while permitting breakage by a surgeon in order to remove frangible plug 74E intraoperatively as described herein.

In examples, the density of the material of porous shell structure 70, frangible plug 74E and struts 76 can be uniform throughout acetabular shell 16. Additionally, in examples, the local density of the material can be selectively varied to include features in porous shell structure 70 and frangible plug 74E. For example, frangible plug 74E can include removal aperture 78E. Removal aperture 78E can comprise an opening in frangible plug 74E that is lined by a denser portion of material than porous shell structure 70. For example, removal aperture 78E can include densified portion 88E that is denser then the remainder of frangible plug 74E. Aperture 78E can be shaped to allow a tool to engage with frangible plug 74E to allow frangible plug 74E to rotated, for example, while densified portion 88E can prevent a tool from stripping out aperture 78E. Densified portion 88E and aperture 78E can, in examples, comprise a hex socket for receiving a mating driver tool. Likewise, each of frangible plugs 74A-74D and 74F-74I can include a removal aperture, although they are not identified for the sake of clarity in FIGS. 5A and 5B.

Port 72E can include densified portion 90E that strengthens port 72E for engagement with struts 76. For example, densified portion 90E can prevent struts 76 from undesirably breaking away portions of porous shell structure 70 when struts 76 are being broken away by the surgeon. However, it can be desirable for the entirety of porous shell structure 70 to not be as dense as densified portion 90E in order to facilitate better bone ingrowth. Additionally, struts 76 themselves can have a different porosity density as compared to porous shell structure 70, densified portion 90E, frangible plug 74E and densified portion 88E in order to better allow for breakage. In examples, the porosity density of struts 76 is less than the porosity density of densified portion 90E.

Sidewall 82 of port 72E can include threading 80 to facilitate assembly of a threaded fastener to porous shell structure 70 after frangible plug 74E is removed. Struts 76 can extend between sidewall 82 and sidewall 84 near the top (with reference to FIG. 5C) of port 72E in order to provide space along sidewall 82 for threading 80. Sidewall 82 can also be shaped to include chamfer 92 to facilitate engagement with the head of a fastener after frangible plug 74E is attached. Frangible plug 74E can include head 94 to mate with chamfer 92 to prevent debris and other matter from passing through port 72E if frangible plug 74E is not removed.

The present subject matter can help provide a solution to various problems associated with prosthetic implants having fixation apertures or ports. Although described with reference to acetabular implants, the frangible plugs, ports, ligaments, struts and other features described herein can be used in other prosthetic implants. For example, orthopedic plates used to repair fractured bones can also include a plurality of apertures having plugs that can be intraoperatively removed based on the anatomy of the specific patient. It can be desirable to have unused apertures or ports in fracture plates be closed-off if not used in order strengthen the plate, as well as for other benefits such as facilitating bone ingrowth, preventing wear debris migration, and preventing bone cement from flowing out of the shell.

The frangible plugs, ports, ligaments, struts and other features described herein can facilitate increasing bone ingrowth capability of porous metal structures by facilitating attachment of porous plugs to openings within the porous metal structure. Thus, more surface area for bone ingrowth is provided. The present disclosure facilitates removal of porous plugs by including crosspiece structures, such as ligaments, rods, struts, webbing and pins, that can be designed to have different strengths, depending on design needs, to provide a strong bond to the porous metal structure to survive implantation and subsequent use within a patient, but that are not so strong that they cannot be readily fractured or otherwise broken to allow intraoperative removal. The frangible plugs, ports, ligaments, struts and other features described herein can, although described with reference to porous structures, be used with non-porous structures. As an example, an opening of a solid metal fracture plate can be connected to a solid metal plug via solid metal struts by integrally manufacturing the fracture plate, plug and struts with a rapid manufacturing process.

Various Notes & Examples

Example 1 can include or use subject matter such as an acetabular shell that can comprise: a cup-shaped body having an interior surface and an exterior surface; a plurality of holes extending from the interior surface to the exterior surface so as to be able to permit fasteners to extend through the cup-shaped body; a plug disposed in each of the plurality of holes to prevent a fastener from extending through each of the plurality of holes; and a plurality of crosspieces connecting each plug to one of the plurality of holes, wherein each crosspiece is comprised of material contiguously defining the cup-shaped body and the plugs.

Example 2 can include, or can optionally be combined with the subject matter of Example 1, to optionally include material that can define the external surface and the internal surface of the cup-shaped body.

Example 3 can include, or can optionally be combined with the subject matter of one or any combination of Examples 1 or 2 to optionally include each of the plurality of crosspieces comprising a frangible strut connecting the cup-shaped body and the plurality of plugs.

Example 4 can include, or can optionally be combined with the subject matter of one or any combination of Examples 1 or 2 to optionally include each of the plurality of crosspieces comprising a ligament.

Example 5 can include, or can optionally be combined with the subject matter of one or any combination of Examples 1, 2 or 4 to optionally include a cup-shaped body comprises a first porous structure; each of the plurality of plugs comprising a second porous structure, the first and second porous structures comprised of a first material; and a second material comprising a layer covering the first and second porous structures and defining the plurality of crosspieces.

Example 6 can include, or can optionally be combined with the subject matter of one or any combination of Examples 1, 2, 4 or 5 to optionally include the first material comprising carbon foam; and the second material comprising tantalum.

Example 7 can include, or can optionally be combined with the subject matter of one or any combination of Examples 1, 2, 4, 5 or 6 to optionally include the second material comprising a chemical vapor deposition layer.

Example 8 can include, or can optionally be combined with the subject matter of one or any combination of Examples 1 or 2 to optionally include the material comprising solidified powder material.

Example 9 can include, or can optionally be combined with the subject matter of one or any combination of Examples 1, 2 or 8 to optionally include the cup-shaped body and the plurality of plugs having a first porosity density of the material; and the plurality of crosspieces having a second porosity density of the material less than the first porosity density.

Example 10 can include, or can optionally be combined with the subject matter of one or any combination of Examples 1 through 9 to optionally include the cup-shaped body being fabricated from porous material between the interior surface and the exterior surface.

Example 11 can include or use subject matter such as an orthopedic implant that can comprise: a structural body comprising: a first surface; a second surface opposing the first surface; and a through-bore extending from the first surface to the second surface, the through-bore having a bore surface; wherein the structural body is formed of a porous material, a plug disposed in the through-bore; and a frangible connection linking the bore surface and the plug.

Example 12 can include, or can optionally be combined with the subject matter of Example 11, to optionally include the plug being formed of the porous material.

Example 13 can include, or can optionally be combined with the subject matter of one or any combination of Examples 11 or 12 to optionally include the frangible connection comprising coating of the structural body and the plug, the coating forming ligaments connecting the porous material of the structural body and the porous material of the plug.

Example 14 can include, or can optionally be combined with the subject matter of one or any combination of Examples 11 through 13 to optionally include the porous material comprising reticulated vitreous carbon foam and the coating comprising tantalum.

Example 15 can include, or can optionally be combined with the subject matter of one or any combination of Examples 11 or 12 to optionally include the frangible connection comprising struts extending between the porous material of the structural body and the plug.

Example 16 can include, or can optionally be combined with the subject matter of one or any combination of Examples 1, 12 or 15 to optionally include the porous material comprising titanium.

Example 17 can include, or can optionally be combined with the subject matter of one or any combination of Examples 11, 12, 15, 16 or 17 to optionally include the bore surface having a higher density of the porous material than the struts.

Example 18 can include or use subject matter such as a method of manufacturing an orthopedic implant, the method comprising: producing a porous structural body having a port; producing a plug for positioning in the port; and producing a plurality of frangible crosspieces within the port to connect the plug to the structural body.

Example 19 can include, or can optionally be combined with the subject matter of Example 18, to optionally include producing the plurality of frangible crosspieces comprises coating the structural body and the plug to form ligaments extending between the structural body and the plug.

Example 20 can include, or can optionally be combined with the subject matter of Examples 18 or 19, to optionally include applying the coating with a chemical vapor deposition process.

Example 21 can include, or can optionally be combined with the subject matter of Example 18, to optionally include producing the plurality of frangible crosspieces comprising integrally forming a plurality of struts with the porous structural body and the plug.

Example 22 can include, or can optionally be combined with the subject matter of Examples 18 or 21, to optionally include the porous structural body, the plug and the plurality of struts being fabricated with an additive manufacturing process.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An acetabular shell comprising:
   a cup-shaped body having an interior surface and an exterior surface, the cup-shaped body comprising a first porous structure;
   a plurality of holes extending from the interior surface to the exterior surface so as to be able to permit fasteners to extend through the cup-shaped body;
   a plug disposed in each of the plurality of holes to prevent a fastener from extending through each of the plurality of holes, each of the plugs comprising a second porous structure, wherein the first porous structure and the second porous structures comprise a first material; and
   a plurality of crosspieces connecting each plug to one of the plurality of holes, wherein each crosspiece is comprised of a second material contiguously defining the cup-shaped body and the plugs;
   wherein the second material comprises a layer covering the first porous structure and the second porous structures such that the plurality of crosspieces comprise ligaments.

2. The acetabular shell of claim 1, wherein the first material defines the external surface and the internal surface of the cup-shaped body.

3. The acetabular shell of claim 1, wherein each of the ligaments of the plurality of crosspieces comprises a frangible strut connecting the cup-shaped body and the plurality of plugs.

4. The acetabular shell of claim 1, wherein:
   the first material comprises carbon foam; and
   the second material comprises tantalum.

5. The acetabular shell of claim 4, wherein the second material comprises a chemical vapor deposition layer.

6. The acetabular shell of claim 1, wherein:
   the cup-shaped body and the plurality of plugs have a first porosity density of the first material; and
   the plurality of crosspieces have a second porosity density of the second material less than the first porosity density.

7. The acetabular shell of claim 1, wherein the cup-shaped body is fabricated from porous material between the interior surface and the exterior surface.

8. An orthopedic implant comprising:
   a structural body comprising:

a first surface;

a second surface opposing the first surface; and a through-bore extending from the first surface to the second surface, the through-bore having a bore surface;

wherein the structural body is formed of a porous material;

a plug disposed in the through-bore, the plug formed of the porous material; and a frangible connection linking the bore surface and the plug;

wherein the frangible connection comprises struts extending between the porous material of the structural body and the plug; and wherein the bore surface is a higher density of material than the struts.

9. The orthopedic implant of claim 8, wherein the frangible connection comprises coating of the structural body and the plug, the coating forming ligaments defining the struts connecting the porous material of the structural body and the porous material of the plug.

10. The orthopedic implant of claim 9, wherein the porous material comprises reticulated vitreous carbon foam and the coating comprises tantalum.

11. The orthopedic implant of claim 8, wherein the porous material comprises titanium.

12. A method of manufacturing an orthopedic implant, the method comprising:

producing a structural body having a first surface, a second surface opposing the first surface and a through-bore extending from the first surface to the second surface, the through-bore having a bore surface, wherein the structural body is formed of a porous material;

producing a plug disposed in the through-bore, the plug formed of the porous material; and producing a frangible connection linking the bore surface and the plug;

wherein the frangible connection comprises struts extending between the porous material of the structural body and the plug; and wherein the bore surface is a higher density of material than the struts.

13. The method of claim 12, wherein producing the frangible connection comprises coating the structural body and the plug to form the struts.

14. The method of claim 13, wherein the coating is applied with a chemical vapor deposition process.

15. The method of claim 12, wherein producing the frangible connection comprises integrally forming the struts with the porous structural body and the plug.

16. The method of claim 15, wherein the structural body, the plug and the struts are fabricated with an additive manufacturing process.

\* \* \* \* \*